United States Patent [19]

Theriot et al.

[11] 4,125,568
[45] Nov. 14, 1978

[54] REMOVAL OF CARBONYL IMPURITIES

[75] Inventors: Walter A. Theriot, New York, N.Y.; Steven D. Saucier; B. M. Drinkard, both of Beaumont, Tex.

[73] Assignee: Mobil Oil Corporation, New York, N.Y.

[21] Appl. No.: 811,106

[22] Filed: Jun. 29, 1977

[51] Int. Cl.² .............................................. C07C 7/10
[52] U.S. Cl. ................................................ 260/681.5
[58] Field of Search .................... 260/681.5 R, 683 R, 260/679

[56] References Cited

U.S. PATENT DOCUMENTS

| | | | |
|---|---|---|---|
| 3,536,775 | 10/1970 | Hutson, Jr. et al. | 260/681.5 R |
| 3,674,887 | 7/1972 | Clay | 260/681.5 R |
| 3,682,779 | 8/1972 | Ritter et al. | 260/681.5 R |
| 3,804,911 | 4/1974 | Liakumovich et al. | 260/681.5 R |
| 3,842,137 | 10/1974 | Libers et al. | 260/681.5 R |

*Primary Examiner*—Veronica O'Keefe
*Attorney, Agent, or Firm*—Charles A. Huggett; Ronald J. Cier

[57] ABSTRACT

Impurities that are carbonyl-containing organic compounds (e.g., acetaldehyde) are removed from organic hydrocarbons produced in conventional production facilities. The process comprises contacting the hydrocarbon product (e.g., butadiene) with an aqueous "scrubbing solution," containing a water soluble reducing agent (e.g., $NaHSO_3$) in slightly greater amount than is theoretically required for complete reaction with the carbonyl compounds, in an in-line mixing means and then passing the mixture to a phase separator to separate the layers. The resulting "scrubbed" hydrocarbon product is substantially purified (e.g., to as low as less than 2 ppm carbonyl compounds). An optional second mixer and scrubbing tower are provided as a back-up system in case of surge conditions or maintenance of the first system.

8 Claims, 1 Drawing Figure

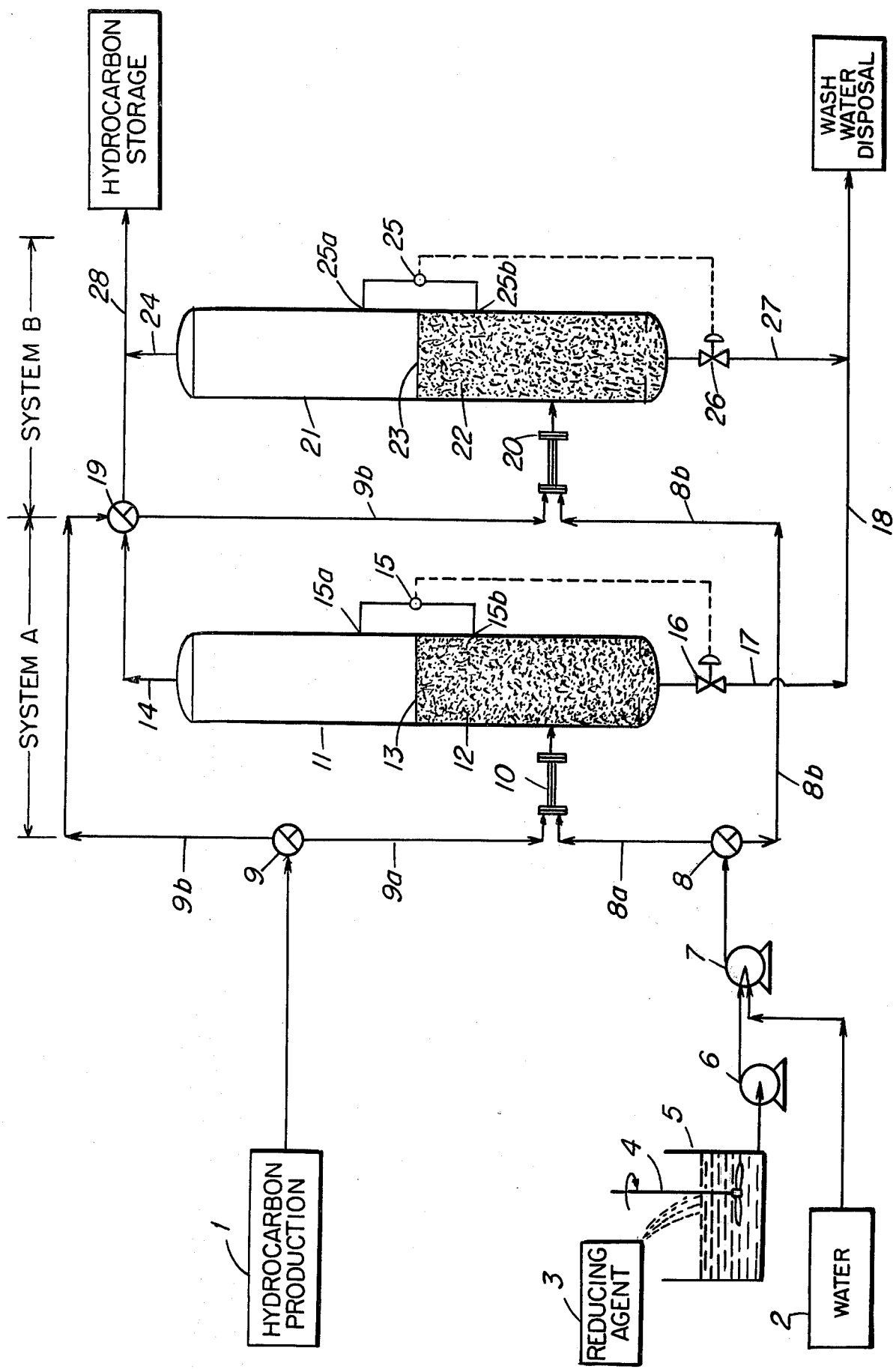

REMOVAL OF CARBONYL IMPURITIES

BACKGROUND OF THE INVENTION

1. Field of the Invention

This invention relates to a process for the removal of carbonyl-containing organic compounds present as impurities in mixture with organic hydrocarbon compounds, and especially to removal of carbonyl compounds from butadiene product streams.

2. Description of the Prior Art

Butadiene is an important industrial chemical. It is used in the manufacture of synthetic rubber, latex paints, and nylon, and is valuable in the Diels-Alder condensation for the synthesis or many diverse compounds. In the synthesis of butadiene, small amounts of carbonyl-containing impurities (e.g., acetaldehyde) are produced and it is important that these impurities be removed or they will have an adverse effect on subsequent processes in which the butadiene is a raw material. Although the carbonyl content of the butadiene product stream is low (it is typically measured in parts per million), the heretofore used procedures for reducing it to an acceptable level of concentration have been undesirably elaborate and expensive.

SUMMARY OF THE INVENTION

It is accordingly an object of the present invention to provide a continuous process whereby the concentration of carbonyl compounds (e.g., acetaldehyde) in the product stream of organic hydrocarbon production (e.g., butadiene) is reduced to a very low level.

It is a further object of this invention to provide a continuous process for removal of such carbonyl compounds which is simple, reliable, and relatively inexpensive.

It is a still further object of this invention to provide a process whereby the carbonyl impurities are removed in a single step, allowing the organic product stream to be sent directly to the usual storage facilities or to subsequent processes without additional clean-up to further reduce the carbonyl content or to remove contaminants left by the washing process.

These and other advantages of this invention will be evident upon consideration of the following specification and claims.

The invention encompasses a process arrangement wherein a continuous stream of such organic hydrocarbon product, bearing the undesired carbonyl-containing compounds, is contacted with an aqueous solution comprising a reducing agent (e.g., sodium bisulfite) suitable for forming on contact a water soluble reaction product with such carbonyl compounds, such reducing agent being in greater and preferably slightly greater concentration than the theoretical stoichiometric ratio for reaction of all of the carbonyl concentration in the organic product on a one-to-one mole basis. For example, an excess of such reducing agent (e.g., sodium bisulfite) will tend to drive the following equilibrium equation to the right:

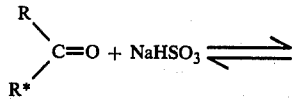

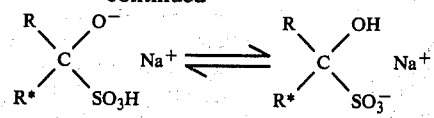

where R is alkyl, alkylene, aryl, aralkyl, etc., and R* is the same as R or is hydrogen, hydroxy, or ester.

To insure good contact in the continuous process as embodied herein, the aqueous solution of the reducing agent and the organic product stream are passed through an in-line mixing zone where they are well mixed. The mixture is then introduced into a phase separating zone where a separation of the aqueous and organic phases occurs. The organic is displaced by the denser water solution already in the separator, the organic material traveling in upward direction until it crosses the interface between the two phases. From the point of entry to the interface, the product is once again contacted with water solution as it migrates toward the interface or, optionally, by means of internal tower packing. The "scrubbed" product continues to rise in the separator and, as overhead from the separator, may be passed to an optional second scrubber which acts as a back-up system in case of surge conditions or maintenance of the first system.

The aqueous layer, containing the absorbed carbonyl-bearing compound, is removed at the bottom of the phase separator by means of an interface level control means. This stream is then fed to a flash pot at the cooling tower and dropped to atmospheric pressure. Any volatile organic material remaining in the stream will flash to vapor form and be removed. The wash water then passes to appropriate disposal means.

BRIEF DESCRIPTION OF THE DRAWING

Understanding of the invention disclosed herein will be facilitated by reference to the single drawing FIGURE, which depicts a flow sheet of a typical process configuration in accord with the invention.

DESCRIPTION OF THE PREFERRED EMBODIMENTS

Referring to the FIGURE, a continuous stream of organic material, in specific embodiment being butadiene in mixture with undesired carbonyl-bearing organic compounds, is supplied directly from production means 1. The organic stream is sent to valve 9 where it is routed either to SYSTEM A via conduit 9a, to SYSTEM B via conduit 9b, or is split, some of it being sent to each system to increase through-put of the overall operation.

The aqueous scrubbing solution is prepared in mixing vat 5 where reducing agent 3 (e.g., sodium bisulfite) is dissolved in water to a convenient concentration. This primary or concentrated scrubbing solution is then pumped out of vat 5 and, if dilution to a lower concentration is necessary, is sent via injection pump 6 to mixing pump 7 where it is diluted to a predetermined concentration of reducing agent by mixing with make-up water 2 and brought to the same pressure as the hydrocarbon product stream from production means 1. The scrubbing solution, which is now at the same pressure as the hydrocarbon product and has a concentration of reducing agent which is 10 to 20% higher then the stoichiometric concentration theoretically required for complete reaction with the carbonyl compounds in the hydrocarbon product, is pumped to valve 8 which directs it to SYSTEM A via conduit 8a or to SYSTEM B via conduit 8b or which splits the stream and sends part of it to each system for simultaneous operation.

Confining the description to SYSTEM A for the moment, the hydrocarbon product (conduit 9a) and the aqueous scrubbing solution (conduit 8a) are introduced into in-line mixing means 10 where they are thoroughly and intimately blended. This mixture is then sent to phase separator 11 for separation of the organic and aqueous phases.

Phase separator 11 is preferably a vertically elongated enclosed container having an overhead outlet means 14 at the top portion for removal of the liquid organic phase and a drain line 17 at the bottom portion for removal of the aqueous phase. Flow of the aqueous phase through drain line 17 is controlled by valve 16, which in turn is operated remotely by interface level control means 15. The phase separator 11 may optionally contain in its lower section a quantity of internal packing material 12 through which the organic/aqueous mixture is percolated while the phases are separating or, alternately, the separator 11 may be empty and the phases allowed to separate without additional percolation. There are many column packing materials which are suitable for this application, a few non-limiting examples being Berl saddles, Intalox saddles and Raschig rings.

The organic/aqueous mixture from in-line mixing means 10 is introduced into the lower portion of phase separator 11. As the organic and aqueous phases in seaparator 11 begins to separate, the organic phase is displaced by the denser aqueous solution. The "scrubbed" organic phase, being of lesser density than the aqueous solution, travels up the phase separator 11 until it crosses the interface 13 between the two phases. From the point of entry into phase separator 11 until it reaches interface 13, the organic product is once again contacted with aqueous solution, such recontact being aided by percolation through packing 12 if such packing is employed. The "scrubbed" product, having now had the major portion of the carbonyl-bearing contaminant removed, continuous to travel up the tower and is taken off overhead at outlet means 14.

Interface level control 15 may be any conventional device for detecting the location of interface 13 between the upper organic phase and the lower aqueous phase. Control 15 is adapted to operate valve 16 such that when the aqueous level in phase separator 11 increases to the point where interface 13 reaches some predetermined level 15a, the valve 16 is opened and separated aqueous solution is drained out of the bottom of separator 11 through drain line 17. When the level of the aqueous phase has been reduced such that interface 13 reaches predetermined level 15b, level control 15 causes valve 16 to be closed. In practice it may be preferable that, instead of level control 15 merely causing valve 16 to be either open or closed, the control be of a type which will continuously regulate the degree of openness relative to the position of interface 13, i.e., the nearer interface 13 is to level 15a the more fully open valve 16 becomes, and the nearer interface 13 is to level 15b the more closed (relatively) valve 16. In some instances, it is desirable that valve 16 be partially open at all times so that there is continuous removal of aqueous phase through drain line 17 at a rate equal to or less then the rate of addition of aqueous phase via conduit 8a. In the latter case, interface level control 15 would serve as a precautionary safety factor should aqueous material enter the phase separator at a rate which is faster or slower than the expected rate. Examples, of suitable control devices would include any conventional interface controller useful for normal service applications.

The in-line mixing means 10 is also of conventional type suitable for admitting two or more streams of unlike materials and continuously mixing them to form a single relatively homogeneous stream. An example of such mixing means would be the KOCH ENGINEERING STATIC MIXER.

The aqueous wash solution removed through drain line 17 is taken via conduit 18 to a suitable in-plant wash water disposal means where it is brought to atmospheric pressure and any absorbed organic material is volatilized. The organic vapors are then either collected and recovered or are sent to suitable disposal means, such as a flare where they are burned. The wash water, containing the reaction products of the carbonyl compounds with the reducing agent and any excess reducing agent, is likewise appropriately disposed of.

The cleaned-up product removed overhead from phase separator 11 at outlet 14 is routed to valve 19 from whence it may take one of two directions. If the carbonyl content is sufficiently reduced and the aqueous phase completely or substantially completely separated, the organic stream is sent through conduit 28 to storage facilities where it is held until required for shipment or subsequent synthetic processes, or it may be sent directly to such subsequent processing steps as deemed necessary. If further scrubbing treatment is desirable, by virtue of requirements to further reduce the carbonyl content of the product or because of incomplete phase separation (for example, as might be caused by surge conditions in SYSTEM A), the overhead stream from outlet 14 is directed into conduit 9b and fed to SYSTEM B.

SYSTEM B is substantially identical to SYSTEM A and serves various purposes. It can be used as a back-up to SYSTEM A in the event of incomplete phase separation therein or the need for further reduction in the carbonyl content of the scrubbed product, or it can serve as a substitute for SYSTEM A to allow for maintenance of that system.

In the event of surge conditions in SYSTEM A, as might result from a sudden and substantial increase in product input or failure of the interface level control 15 and/or drain valve 16 to function properly, thereby causing incomplete phase separation such that the overhead stream being removed at outlet 14 undesirably contains aqueous material as well as organic material, the overhead stream is redirected by means of valve 19 through line 9b and into phase separator 21 where separation and removal of the aqueous phase takes place. The scrubbed organic phase is then taken off at outlet 24 and sent through conduit 28 to the appropriate storage facilities.

Should it become necessary to further reduce the carbonyl content of the "scrubbed" organic product after initial treatment in phase separator 11, for instance because of some especially stringent requirement or because SYSTEM A has for some reason not functioned efficiently enough to meet the usual product specification, the organic stream is redirected through line 9b as above and, together with fresh aqueous scrubbing solution from line 8b, is fed into in-line mixing means 20. The subsequent mixing and phase separation are the same as those described with respect to SYS- TEM A. The scrubbed organic product is taken off overhead at outlet 24 and sent to storage.

At those times when it becomes necessary to shutdown SYSTEM A entirely, as when performing preventive maintenance procedures or replacing malfunctioning equipment, SYSTEM B can be substituted without interruption of the scrubbing operation. To accomplish this the organic product is simply rerouted, by means of valves 9 and 19, through line 9b while the aqueous scrubbing solution is rerouted through line 8b by means of valve 8. SYSTEM A is then completely out of the stream and readily accessible to maintenance personnel while SYSTEM B carries the full output from production means 1.

Non-limiting examples of organic hydrocarbons, the production product of which is likely to contain an impurity of carbonyl compounds and which are amenable to the instant process for the removal of such impurity, include any hydrocarbon in the $C_4$-$C_5$ range which is the product of the pyrolysis of other organic compounds. Especially preferred is butadiene.

Compounds suitable for use as reducing agents in the instant process include: metallic (e.g., sodium) bisulfite; hydrazine; hydroxylamine; phenylhydrazine; and the like, which are water soluble and form water soluble reaction products on contact with carbonyl-bearing organic compounds dissolved in organic medium.

EXAMPLE

Butadiene, containing 300 ppm carbonyl (as acetaldehyde), is supplied in a continuous stream from conventional production facilities. Such a stream, at a pressure of 159 psia and a temperature of 29°-32° C. (85°-90° F.), enters the system as illustrated in the drawing.

Aqueous scrubbing solution, containing 4-5 wt. % sodium bisulfite, is pumped from vat 5 to pump 7, where it is diluted to 700-900 ppm sodium bisulfite with additional water. This dilute scrubbing solution is then pumped to SYSTEM A at a pressure of 120 psia and ambient temperature.

The two streams are blended in the in-line KOCH STATIC MIXER 10, in proportions resulting in a mixture having a mole ratio of reducng agent to carbonyl compound of 1.1:1 to 1.2:1, and the mixture fed into the lower portion of the phase separator 11 where the organic and aqueous phases are separated (without the use of the optional packing 12) at 125 psia and 27° C. (80° F.).

The resulting "scrubbed" butadiene product is taken off overhead via outlet 14 from the phase separator and has a carbonyl content (as acetaldehyde) of < 2 ppm. It is then sent directly to the normal storage facilities to await appropriate disposition.

The used wash water is drained from the bottom of the phase separator 11 by means of a drain valve 16, controlled by conventional level control device 15, fed to a flash pot and dropped to atmospheric pressure. Any volatile organic material in the water solution is flashed off and fed to a plant flare system to be burned or is otherwise disposed of. The water is pumped into a cooling tower basin.

The example and embodiments described herein are for illustrative purposes only and it is not intended thay they be limiting in any way on the concept disclosed. Various changes and modifications may be made without departing from the spirit and scope of the invention, as will be readily apparent to one skilled in the art, and such changes and modifications are intended to be within the scope of the appendant claims.

Having thus described our invention, we claim:

1. A method of removing carbonyl compounds present as impurities in the product stream of unsaturated $C_4$ and $C_5$ hydrocarbon production, said method comprising:
   (a) mixing in an in-line mixing zone said product stream containing said carbonyl impurities with an aqueous solution of a reducing agent that reacts with carbonyl compounds to form water soluble reaction products therewith, the resulting mixture of the hydrocarbon product stream and aqueous solution containing therein said reducing agent in an amount in excess of the theoretical stoichiometric amount required to effect complete reaction of said reducing agent and said carbonyl impurities;
   (b) passing the resulting mixture from said in-line mixing zone to a phase separating zone wherein the organic phase of said mixture is substantially separated from the aqueous phase of said mixture, thereby providing:
      (1) an aqueous phase comprising a water solution of the reaction products of said reducing agent with said carbonyl impurities along with unreacted reducing agent, and
      (2) an organic phase comprising the unsaturated hydrocarbon product; and
   (c) withdrawing said separated organic phase from said phase separating zone as an organic phase having significantly reduced content of said carbonyl impurities as compared to the original hydrocarbon product stream containing said impurities.

2. A continuous process for extraction of carbonyl-bearing compounds contained in small amount in the product stream of unsaturated $C_4$ and $C_5$ hydrocarbon production, said process comprising:
   (a) contacting said hydrocarbon product stream containing said carbonyl-bearing compounds with an aqueous solution of a reducing agent that reacts with carbonyl-bearing compounds to form water soluble reaction products therewith;
   (b) blending said hydrocarbon product stream and said aqueous solution in an in-line mixing means;
   (c) passing the mixture of said hydrocarbon product with said aqueous solution to the lower portion of a phase separating means for separation of the aqueous phase of said mixture from the hydrocarbon phase of said mixture, said separating means comprising:
      (1) a vertically elongated, enclosed container having an outlet in the top portion thereof for removal of liquids from the top of said container, a valved outlet in the bottom portion thereof for removal of liquids from the bottom of said container, inlet means in the lower portion thereof to admit liquid mixture from said in-line mixing means, and an interface level control means for detecting the level of the interface between the separated aqueous and hydrocarbon phases, said control means being connected to and controlling the opening and closing of said valved outlet such that when said interface rises above a predetermined level in said container, said valved outlet is opened to drain out a portion of the separated aqueous phase and when said interface drops below another predetermined level said valved outlet is closed to stop or reduce the removal of said separated aqueous phase;

(d) separating the hydrocarbon phase from the aqueous phase of said mixture such that as said hydrocarbon phase is displaced upwardly in said phase separating means it is continually brought into contact again with said aqueous phase, as said aqueous phase migrates downwardly, until said hydrocarbon phase reaches the interface between the separated hydrocarbon layer and separated aqueous layer;

(e) withdrawing the separated hydrocarbon phase from said outlet at the top portion of said phase separating means, said separated hydrocarbon phase having reduced content of said carbonyl-bearing compounds relative to said hydrocarbon product stream; and (f) withdrawing the separated aqueous phase from said valved outlet at the bottom portion of said phase separator.

3. The continuous process of claim 2 further comprising an internal packing material in the lower section of said separating means through which said liquid mixture from said in-line mixing means is percolated to increase the contact between said hydrocarbon phase and said aqueous phase while said phases are separating into distinct layers.

4. The continuous process of claim 2 further comprising performing a second extraction on said separated hydrocarbon phase, said second extraction being similar to the first extraction and further reducing the content of said carbonyl-bearing compounds in said hydrocarbon phase.

5. The process of claim 2 wherein said unsaturated hydrocarbon is butadiene.

6. The process of claim 2 wherein said reducing agent in said aqueous solution is a metallic bisulfite compound.

7. The process of claim 6 wherein said metallic bisulfite is sodium bisulfite.

8. The process of claim 2 wherein said reducing agent is present in said mixture of said hydrocarbon product with said aqueous solution in an amount which is from 10 to 20% greater than the theoretical stoichiometric amount required to react with all of said carbonyl-bearing compounds on a one-to-one mole basis.

* * * * *